United States Patent [19]

Greco et al.

[11] Patent Number: 5,116,619

[45] Date of Patent: May 26, 1992

[54] VAGINAL PROGESTERONE TABLET

[75] Inventors: John C. Greco, 120 Country Club La., Mamou, La. 70554; James W. McGinity, Austin, Tex.

[73] Assignees: Lee Roy Morgan; John C. Greco, both of New Orleans, La.

[21] Appl. No.: 238,535

[22] Filed: Aug. 30, 1988

[51] Int. Cl.$^5$ .................... A61K 9/02; A61F 13/00
[52] U.S. Cl. .................... 424/433; 424/430; 424/432; 424/434; 424/470; 424/469; 514/843; 514/935; 514/967; 514/177; 514/777
[58] Field of Search .................... 424/484–488, 424/430–433, 434, 465, 469, 470

[56] References Cited

U.S. PATENT DOCUMENTS

| | | | |
|---|---|---|---|
| 3,656,483 | 4/1972 | Rudel | 128/264 |
| 4,228,797 | 10/1980 | Dickey | 128/270 |
| 4,565,694 | 1/1986 | Kovacs et al. | 424/80 |
| 4,585,782 | 4/1986 | Plempel et al. | 514/396 |
| 4,587,267 | 5/1986 | Drake et al. | 514/769 |
| 4,650,665 | 3/1987 | Kronenthal et al. | 424/484 X |
| 4,814,183 | 3/1989 | Zentner | 424/485 |

FOREIGN PATENT DOCUMENTS

2155330  8/1985  United Kingdom .

OTHER PUBLICATIONS

Steege, J. F., "Bioavailability of Nasally Administered Progesterone", *Fertility and Sterility*, 46–4:727–729 (1986).

Fulper, L. D., et al., "Comparison of Serum Progesterone Levels In Dogs After Administration of Progesterone By Vaginal Tablet and Vaginal Suppositories", *AM.J. Obstet. Gynecol.*, 156:253–256 (1987).

Price, J. H., et al., "Effect of the Suppository Base on Progesterone Delivery from the Vagina", *Fertility and Sterility*, 39–4:490–493 (1983).

Ritter, W., "Pharmacokinetic Fundamentals of Vaginal Treatment with Chlotrimazole", *AM. J. Obstet. Gynecol.*, 152:945–947 (1985).

Kennedy, J. H., et al., "Induction of Labour: A Comparison of a Single Prostaglandin E$_2$ Vaginal Tablet with Amniotomy and Intravenous Oxytocin", *British Journal of Obstetrics and Gynaecology*, 89:704–707 (1982).

Back, D. J., et al., "Comparative Pharmacokinetics of Levonorgestrel and Ethinyloestradiol Following Intravenous, Oral and Vaginal Administration", *Contraception*, 36–4:471–9 (1987).

Lebhertz, T. B., et al., "A Comparison of a Three-Day and Seven-Day Clotrimazole Regimen for Vulvovaginal Candidiasis", (citation currently unavailable, but will be provided upon request).

Meyers, E. R., et al., "Serum Progesterone Levels Following Vaginal Administration of Progesterone During the Luteal Phase", *Fertility and Sterility*, 47–1:71–75 (1987).

Meirik, O., et al., "Plasma Concentrations of Chloroquinaldol (Sterosan®) after Administration of a Vaginal Tablet", *Gynecol. Obstet. Invest.*, 9:166–169 (1978).

(List continued on next page.)

*Primary Examiner*—Thurman K. Page
*Assistant Examiner*—James M. Spear
*Attorney, Agent, or Firm*—Klarquist, Sparkman, Campbell, Leigh & Whinston

[57] ABSTRACT

A vaginal progesterone suppository is provided in the form of a tablet which delivers biologically effective amounts of progesterone for at least about 48 hours, and blood amounts above basal levels for 72 hours. The tablet is formulated to preferably have a hardness on its edge of 8–13 kg, and disintegrates from its surface to form a milky suspension in 6–8 hours after it is inserted in the vaginal vault. The tablet contains, by weight, about 13–20% progesterone, 65–85% lactose, 2–10% corn starch paste binder, 3–10% corn starch disintegrant, and 0.1–0.9% magnesium stearate as a lubricant. The ratio by weight of progesterone to lactose is preferably 1:6, and the ratio of starch paste binder to starch disintegrant is preferably 1:1. This dosage form is an effective treatment for many progesterone deficiency conditions, and provides enhanced bioavailability.

34 Claims, 1 Drawing Sheet

OTHER PUBLICATIONS

Spatling, L., et al., "Influence of Different Prostaglandin Applications on Cervical Rheology", *Int. J. Gynaecol. Obstet.*, 23:269-376 (1985).

Sato, T., et al., "Plasma, Progesterone and Prostaglandin $F_{2-alpha}$ Levels During the Insertion of Prostaglandin $F_{2-alpha}$ Vaginal Tablets", *Prostaglandins,* 4–1:1-07-113 (1973).

Ishihama, A., et al., "Clinical Field Test of a New Contraceptive Vaginal Foam Tablet", *Contraception,* 6–5:4-01-410 (1972).

Frerich, W. et al., "The Frequency of Candida Infections in Pregnancy and Their Treatment with Clotrimazole", *Curr. Med. Res. Opin.,* 4–9:640-644 (1977).

An information summary entitled "Suppositories and Other Rectal, Vaginal, and Urethral Preparations", pp. 342-358 (citation data unknown, at this time, but will be provided upon request).

Begum, S. F., et al., "A Clinical Trial of Neo Sampoon Vaginal Contraceptive Tablets", *Contraception,* 22–6:5-73-582 (1980).

Kjaeldgaard, A., "Comparison of Terconzazole and Clotrimazole Vaginal Tablets in the Treatment of Vulvovaginal Candidosis", *Pharmatherapeutica,* 4–8:5-25-531 (1986).

Lolis, D., et al., "Double-Bind Evaluation of Miconazole Tampons, Compared with Clotrimazole Vaginal Tablets, in Vaginal Candidiasis", *Clinical Therapeutics,* 4–3:212-216 (1981).

Information summary entitled "Peroral Solids, Capsules, Tablets, and Controlled-Release Dosage Forms", pp. 141-177 (specific citation not available at this time, but will be provided upon request).

Product literature from 1973 Physician's Desk Reference describing Gyne-Lotrimin ® clotrimazole vaginal tablets which contain 100 mg clotrimazole dispersed in a variety of materials including cornstarch.

Excerpt from the U.S. Pharmacoepeia (XXI) p. 1242.

Data sheets listing a variety of abstracts located during a computer search on the present invention.

Morgan, L. R., et al., "A Vaginal Pregesterone Tablet: Its Use in Amenorrhea and Dysfunctional Uterine Bleeding", (Abstract) *The Journal of Clinical Pharmacology,* Sep. 1987 Issue, vol. 27, No. 9.

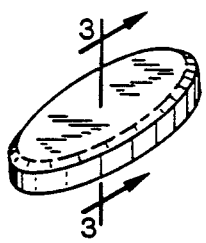
FIG. 1
FIG. 2

FIG. 4
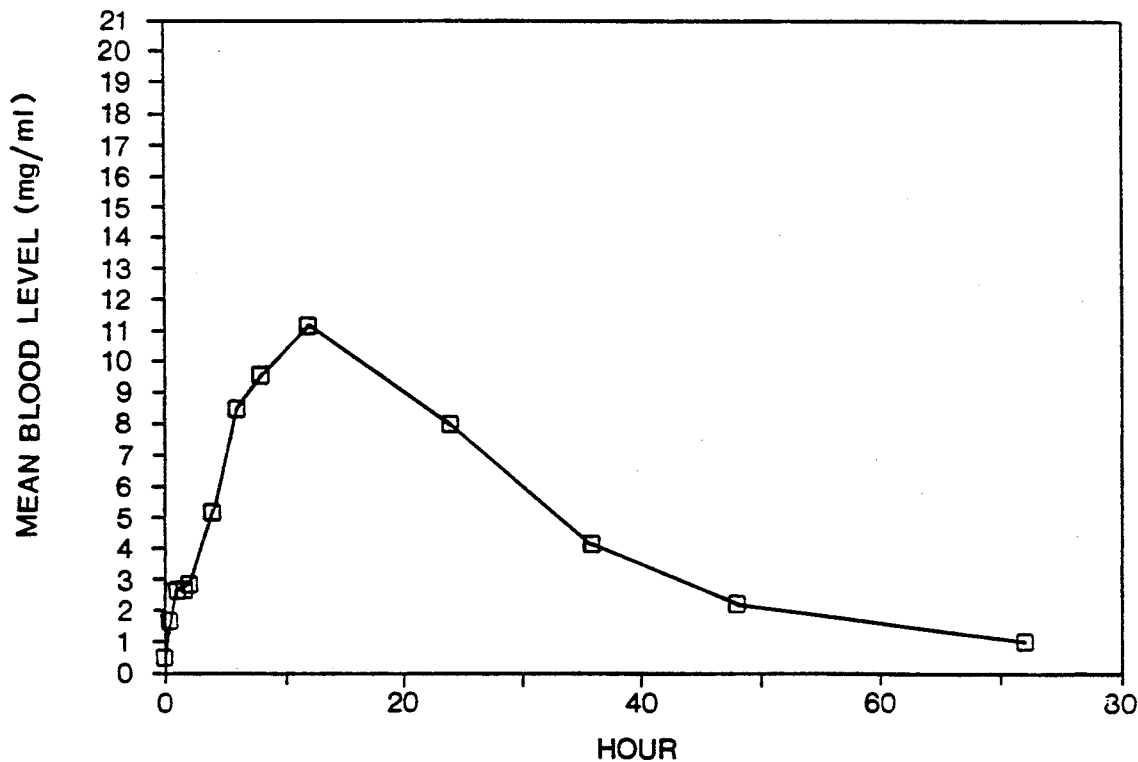
BIOAVAILABILITY STUDY FOR A
SINGLE 200 MG PROGESTERONE VAGINAL TABLET
(MEAN FOR 6 PATIENTS)

VAGINAL PROGESTERONE TABLET

BACKGROUND OF THE INVENTION

1. Field of the Invention

The invention relates to vaginal suppositories and methods of intra-vaginal delivery of drugs. More particularly, it concerns treatment of progesterone deficiency conditions with a vaginal tablet or insert.

2. General Discussion of the Background

The major biologic functions of progesterone are to prepare the uterine endometrium for fertilization and implantation and to support pregnancy. In addition, progesterone has the ability to inhibit the rhythmic contractions attributed to the natural spontaneous contractile properties of the myometrial layer of the uterus.

The secretion of progesterone by the ovary begins just prior to ovulation from the follicle that is destined to release an ovum. After ovulation, the follicle becomes the corpus luteum, which is the primary source of endogenous progesterone. Progesterone converts estrogen primed proliferating endometrial cells of the uterus into mature secretory cells. During this conversion, mature endometrial cells and glands are produced, along with blood vessels and carbohydrates necessary to support a fertilized ovum if conception occurs. If conception does not occur, the corpus luteum regresses and progesterone production decreases. This leads to necrosis of the endometrial cells and glands with sloughing of the epithelial layer of the endometrium.

During normal formation of the uterine endometrium within menstrual cycle, estrogens are necessary for cellular proliferation and progesterone is needed for maturation and secretory gland formation. An estrogen stimulated proliferative endometrium must be present for progesterone to induce a secretory endometrium. If an estrogen primed proliferative endometrium does not proceed to a secretory phase, it usually is because of anovulation and insufficient progesterone production. If insufficient progesterone exists, then minimal to no secretory epithelium is formed and menstrual bleeding is incomplete or does not occur.

The natural secretion of progesterone is 1-2 mg/day during the follicular phase of the menstrual cycle. During the luteal phase, the rate of secretion increases to 10-20 mg/day. The reference serum levels for progesterone are 0.1-1.5 ng/ml for the follicular phase and 2.5-28.1 ng/ml for the luteal phase. For mid-luteal phase, values of 5.7-28.1 ng/ml are reported. In the later stages of pregnancy, the secretion is several hundred mg/day of progesterone.

Inactivation of progesterone takes place largely in the liver. While most of the metabolites of progesterone are unidentified, one of the major urinary products is the glucuronide of pregnane-3a,20a-diol. About 50 to 60% of administered radiolabeled progesterone appears in the urine and about 10% in feces. Pregnanediol in urine accounts for 12 to 15% of the progesterone metabolized.

The rate of turnover of endogenous progesterone is rapid, the plasma half-life being a few minutes. The half-life of progesterone after intravenous injections has two phases. The first half-life is 5-6 minutes and the second is 42-45 minutes. A small amount of progesterone is stored in body fat, but this is generally regarded as quantitatively unimportant.

In the absence of organic pathology, such as submucous fibroids, uterine cancer, or infections, the infrequency or absence of the menstrual bleed usually results from abnormalities in the production of estrogen and/or progesterone. Such conditions are usually referred to as amenorrhea or functional uterine bleeding. It is usually impossible to reduce the issue of the etiology of abnormal menstrual function, to a single factor except in disease states such as pituitary tumors. The following can alter the production of progesterone and result in progesterone deficiency conditions:

1. Ovarian Failure. Hypergonadotrophic hypogonadism, or the inability of the ovary to respond to any gonadotrophic stimulation, is usually due to the absence of follicular tissue on a genetic basis.

2. Central Failure. Hypogonadotrophic hypogonadism, involves hypothalamic or pituitary suppression expressed in low serum gonadotrophins.

3. Anovulatory Dysfunction. The patient who has asynchronous gonadotrophin and estrogen productions and does not ovulate can present with a variety of clinical manifestations. The associated clinical signs and symptoms depend upon the level of gonadal function preserved. Lack of or infrequent menstrual bleeds is a common finding.

By definition, amenorrhea is the failure to menstruate. It is a symptom rather than a disease and has many possible causes. Amenorrhea can result from disturbed reactions anywhere in the hypothalamic-pituitary-ovarian-uterine axis, with or without an associated organic lesion. Any patient who has a history of previously menstruating, but who now has absence of menstrual bleeding with a negative pregnancy test, is usually evaluated for the clinical problem of amenorrhea.

The normal ovulatory function of the menstrual system relies on a dynamic coordination of complex actions. Thus, a minor deficiency in the estradiol signal may be associated with a subnormal central response and an impaired or inappropriate degree of follicular growth and function. Dysfunction is sustained by abnormal fluctuations in the internal feedback mechanisms within the hypothalamic—pituitary—ovarian systems, and functional uterine bleeding may become a persistent problem. This usually results in erratic menstrual bleeding patterns.

Thus, failure to menstruate or infrequent or incomplete menstrual bleeding, in the absence of pathology, is usually associated with insufficient quantities of estrogens to initiate the proliferative phase of the endometrium and/or the absence of progesterone to convert estrogen-primed endometrium into a mature decidual epithelium with secretory glands and cells. The latter transformation to a mature epithelium must occur prior to any type of sloughing. The sloughing and concomitant bleeding is recognized as menstruation. Absence of endometrial maturation under the influence of progesterone results in amenorrhea.

The commonly employed routes of progesterone administration have limitations (Steege et al., *Fertil. Steril.* 46:727-729 (1986)). Absorption of orally administered micronized progesterone is influenced by stomach contents, first-pass liver metabolism and other unknown factors, resulting in significant but highly variable serum levels, thus reducing the therapeutic usefulness of oral progesterone. These problems with oral administration are sometimes avoided by using synthetic progestins. The absorption of progesterone by the rectal route is influenced by the first-pass effects of the liver and absorption is highly variable, thus limiting that pathway of administration. Parenteral administration requires deep intramuscular injections which are often very painful and irritating at the site of injection. Although parenteral administration permits the use of natural hormones rather than progestins, variations in peak plasma levels require dosages of 5 to 10 mg daily for 6 to 8 days.

Since progesterone is absorbed via the vaginal epithelium and it is not commercially available as a vaginal preparation, pharmacists routinely compound fatty acid and cocoa butter progesterone suppositories for patient use. Unfortunately, these suppositories are expelled from the vagina by coughing or sneezing. Moreover, the suppository quickly melts, which allows it to leak out of the vagina and soil a patient's clothing. The rapid dissolution of these prior vaginal suppositories has also greatly reduced their bioavailability.

A contraceptive vaginal tablet is disclosed in U.S. Pat. No. 4,565,694. It contains boric acid, tartaric acid, vitamin $K_3$, a lubricant and sufficient disintegrants to disintegrate quickly after vaginal insertion. Quick dissolution of the tablet allows dispersal of its spermicidal contents, but greatly reduces the bioavailability of any drug contained in the tablet.

U.S. Pat. No. 4,585,782 discloses a vaginal tablet for rapidly dispersing an antimycotic composition. The composition is formulated to reduce the pH of the formulation to about 3-6. This low pH greatly increases the rate of release of the entire composition. Unfortunately, sustained release of a drug is not possible with such a tablet. Bioavailability of the drug is therefore reduced.

It is therefore an object of this invention to provide a vaginal tablet having prolonged bioavailability.

It is another object of this invention to provide such a tablet which is suitable for treating progesterone deficiency conditions.

Yet another object of the invention is to provide a vaginal suppository in which the pharmaceutically active component is retained within the vagina.

SUMMARY OF THE INVENTION

These and other objects of the invention are achieved by a vaginal tablet which contains progesterone and a carbohydrate in sufficient amounts to deliver biologically effective amounts of progesterone for at least about 48 hours, and preferably 72 hours, after the tablet is inserted into a human vagina. The tablet is formulated to have a hardness on its edge in the 8 to 13 kg range, most preferably 9-10 kg, such that the tablet disintegrates from its surface after insertion into the low moisture environment of the vagina. Within about 6-8 hours, the tablet disintegrates completely and forms a micronized, milky suspension which dissolves in the vaginal fluids. The micronized tablet is retained in the vaginal fluids and absorbed through the vaginal epithelium for a prolonged period of time.

The tablet contains a therapeutic amount of progesterone, an excipient, and a disintegrant. The excipient is preferably lactose, while the disintegrant is preferably a carbohydrate, preferably starch, especially corn starch. It is also desirable to add a lubricant, such as magnesium stearate, in amounts less than 1% by weight.

The vaginal tablet contains about 13-20% progesterone, 65-85% lactose, 2-10% starch paste, 3-10% corn starch, and 0.1-0.9% magnesium stearate, preferably 12-14% progesterone, 78-81% lactose, 2-4% starch paste, 2-4% corn starch, and 0.4-0.6% magnesium stearate, and most preferably 13.5% progesterone, 79% lactose, 3.5% starch paste, 3.5% corn starch, and 0.52% magnesium stearate.

In preferred embodiments, the tablet includes about 7% starch by weight, most preferably about 3.5% starch by weight as a binder and about 3.5% starch by weight as a disintegrant. The lactose and progesterone are contained in a granule, and the disintegrant surrounds the granule. A lubricant, such as magnesium stearate, is also included in the tablet.

In especially preferred embodiments, the vaginal tablet includes, by weight, about 13.5% progesterone, 79% lactose, 7% corn starch (3.5% as a binder and 3.5% as a disintegrant), and 0.5% lubricant such as magnesium stearate. The progesterone is micronized such that the majority of the particles, preferably at least 80%, are less than about a micron in diameter. The lactose and starch particles should be less than about 50 microns in diameter. These fine particle sizes provide comfort to the patient, and increase the surface area of the drug such that it goes into solution quickly. The small particle sizes pass more easily through the vaginal epithelium than do larger particles.

The ratio of progesterone to lactose is preferably about 1:6 to provide optimum disintegration with sustained bioavailability of the progesterone. The ratio of binder to disintegrant is also preferably about 1:1. Optimum disintegration of the tablet in the vagina is usually obtained if a tablet disintegrates in 4-6 minutes using the disintegration test (701) described in USP XXI.

The invention also includes a method of making a vaginal tablet by forming a wet granulation of a therapeutic amount of progesterone, a filler excipient, and a binding agent for binding the progesterone and excipient. The granulation is then dried to form dry granules, which are then blended with a disintegrant in sufficient amounts to form a tablet which delivers biologically effective amounts of progesterone for at least about 48 hours, and preferably about 72 hours, after the tablet is inserted into a human vagina. In preferred embodiments, the dry granules and disintegrant are also blended with a lubricant and compressed into a diamond shaped tablet which is retained within the vagina. In especially preferred embodiments, the diamond shaped tablet is 2.5 cm long, 1.3 cm wide, and 0.5 cm thick for maximum retention.

The vaginal tablet is suitable for treating a variety of progesterone deficiency conditions such as menstrual irregularities (amenorrhea), functional uterine bleeding, luteral phase defects, premenstrual tension, in osteoporosis therapy, infertility, ovarian failure, hypogonadotrophic hypogonadism, and anovulatory dysfunction.

BRIEF DESCRIPTION OF THE DRAWINGS

FIG. 1 is a top perspective view of a vaginal tablet made in accordance with the present invention.

FIG. 2 is a top view of the tablet of FIG. 1.

FIG. 4 is a graph showing mean bioavailability of progesterone from a single 200 mg progesterone vaginal tablet made in accordance with the present invention.

DETAILED DESCRIPTION OF PREFERRED EMBODIMENTS

Figure 3:
FIG. 3 is a cross sectional view of the tablet taken along lines 3—3 of FIG. 1.

The present invention is a solid dosage form of progesterone that disintegrates by a surface erosion mechanism. This dosage form was developed for intravaginal use to treat gynecological problems characterized by progesterone deficiency, such as amenorrhea, functional uterine bleeding, luteal phase defects, premenstrual tension, and infertility, as well as in osteoporosis therapy. It has been found that these conditions respond much better to prolonged administration than to the quick release vaginal tablets of the prior art which delivered drugs other than progesterone.

The tablet is preferably formulated to erode in the vagina during a 6 to 8 hour period. The eroding tablet produces micronized particles of the drug which are dispersed in the vagina as a milky suspension along with the other ingredients in the tablet. These micronized particles are retained in vaginal fluids for about 48–72 hours, during which time sustained bioavailability of progesterone is attained. Production of the micronized particles of the milky suspension requires careful selection of the filler excipient. Typical excipients such as microcrystalline cellulose, calcium sulfate, and directly compressible sugars such as sucrose, dextrose and fast-flo-lactose are unsuitable for producing the fine, milky suspension of progesterone. These unsuitable excipients produce a gritty suspension that is uncomfortable to the patient and results in reduced bioavailability of progesterone.

The optimization of disintegration times for vaginal tablets is quite different from more traditional theoretical and practical approaches that are utilized for oral dosage forms. The tablet excipients, for example, employed in oral dosage forms cannot be included in the vaginal delivery system of the present invention. The differing amounts of moisture present in the mouth and vagina are primarily responsible for the different approaches required in these two regions. Although large amounts of "super disintegrants" can explode tablets very quickly in moist environments such as the mouth, the present inventors have determined that super disintegrants in a vaginal tablet turn the tablet into a sponge-like mass following vaginal insertion. A milky suspension is not formed, and drug absorption is retarded. Smaller amounts of the super disintegrants cause a gelatinous sheath to form around he tablet, which inhibits further tablet disintegration and thereby reduces drug bioavailability. The present invention avoids these problems by using a starch disintegrant, particularly corn starch, instead of the super disintegrants of the prior art. Examples of such unsuitable prior art super disintegrants are cross-linked polyvinylpyrrolidine, sodium starch glycolate, or croscarmellose at the 2–4% level.

In addition to the choice of disintegrant, the selection of the binder or adhesive is extremely important. Corn starch paste was found to be the superior binding agent in the present invention, followed by polyvinylpyrrolidine. These agents were found to be superior to more traditional binding agents such as acacia, gelatin, sodium alginate and other gum like agents. The binder allows the progesterone and lactose to bind to one another, which renders the progesterone more hydrophilic and capable of moving through the vaginal epithelium.

Other starches besides corn starch can be used as the disintegrant or binder. Examples of such other starches are rice starch, wheat starch, and potato starch.

The optimum formulation and methods of manufacture and use of the tablet are disclosed in the following examples.

EXAMPLE 1

The optimum tablet formulation containing 200 mg of progesterone is, by weight:

| | |
|---|---|
| Progesterone, USP | 13.50% |
| Lactose, USP (filler excipient) | 79.00% |
| Corn starch paste (binder) | 3.49% (dry weight) |
| Corn starch (disintegrant) | 3.49% |
| Magnesium stearate, USP (lubricant) | 0.52% |

The progesterone USP was a micronized powder obtained from the Upjohn Company. More than 50% of the micronized particles had diameters less than about one micron. Preferably about 80% of the particles should have diameters less than a micron. The physical and chemical characteristics of the progesterone were:
1. Chemical Name: Progesterone; pregn-4-ene-3,20-dione; 4-pregnene-3,20-dione
2. International Nonproprietary Name: Progesterone
3. Empirical Formula: $C_{21}H_{30}O_2$
4. Structural Formula:

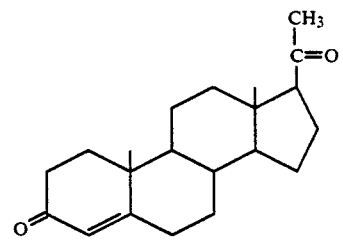

The lactose was obtained in a powdered form from Sheffield Products under the product name Lactose Hydrous USP. The diameters of the lactose particles in the powder were less than about 50 microns.

The corn starch was obtained in a powdered form from Staley Mfg. Co. under the product name Corn Starch USP. The diameters of the starch particles in the powder were less than about 50 microns.

Magnesium stearate was obtained from Mallinckrodt, Inc. under the product name Magnesium Stearate USP.

EXAMPLE 2

The tablet of Example 1 was manufactured in the following manner.

The lactose and the progesterone were mixed in a V-blender for 15 minutes and then transferred to a Hobart mixer. The starch paste was added to the lactose:-progesterone blend to prepare the granulation. The starch paste was at an 18% w/v percentage in the optimized product. The damp mass was then passed through a number 12 screen and the granules were dried for three hours at 50° C. The moisture content at this stage was less than 1%. The granules were then passed through a 20 mesh screen and weighted. The corn starch which had previously been screened through a 60 mesh screen was blended in with the dry granules for five minutes and the pre-screened magnesium stearate was then added to the granules and blended for an additional four minutes. The corn starch powder and the magnesium stearate were adjusted on the basis of the percent yield of dry granules and the moisture content, to ensure that the percent of ingredients in the finished dosage form was the same as the percentages listed in the above formula. The dry granules were then compressed into hard pressed, diamond shaped white tablets with bevelled edges, as shown in FIGS. 1-3. The tablet was 2.5 cm long, 1.3 cm at its maximum width, and 0.5 cm thick. The edges on both flat surfaces were bevelled at 45° angles, with 0.1 cm reduction in height, width and length on all edges.

The tablet hardness for a diamond shaped tablet on its edge was in the 8 to 13 kg range, with 9 to 10 being the most desirable. Tablets that exceeded the 13 kg hardness level gave a slower disintegration time in vivo, which reduced progesterone blood levels in vivo.

Tablet hardness was determined by a Haberlein hardness tester. The tablet is placed flat on a surface and compressed between a pair of plates which measure the maximum compression force on the tablet when it disintegrates.

Tablet disintegration time in water was 4-6 minutes using USP XXI Physical Test (701) for disintegration of an uncoated tablet. Disintegration time in the vagina was 6-8 hours.

EXAMPLE 3

Although optimum results are obtained with the formulation of Example 1, other vaginal tablets were prepared and tested having ingredients in the following ranges:

| Progesterone, USP | 13-20% |
| Lactose, USP | 65-85% |
| Starch paste | 2-10% (dry weight) |
| Corn starch | 3-10% |
| Magnesium stearate, USP | 0.10-0.9% |

Specific formulations are given in the following Examples 4-6 in which the corn starch paste was prepared by mixing the corn starch with 40 ml of water. The progesterone and paste were then wet granulated and dried in open air overnight. The granulation was then combined with the corn starch disintegrant and powdered lactose, then mixed in a blender for 10 minutes. The magnesium stearate was added, and the granulation was then mixed an additional 4 minutes. The tablet hardness range for each of Examples 4-6 was 10-12 kg. Each of the tablets disintegrated in less than 43 seconds in a beaker using the USP XXI (Physical Test 701) disintegration test for uncoated tablets.

EXAMPLE 4

|  |  | g/tablet |
|---|---|---|
| Progesterone | 15.38% | 0.199 |
| Lactose Q.S. | 76.02% | 0.989 |
| Starch paste | 4% | 0.052 |
| Corn starch | 4% | 0.052 |
| Magnesium stearate | 0.6% | 0.0078 |
| Tablet weight |  | 1.3 |

EXAMPLE 5

|  |  | g/tablet |
|---|---|---|
| Progesterone | 14.28% | 0.199 |
| Lactose Q.S. | 77.8% | 1.0894 |
| Starch paste | 3.71% | 0.0519 |
| Corn starch | 3.71% | 0.0519 |
| Magnesium stearate | 0.56% | 0.0078 |
| Tablet weight |  | 1.4 |

EXAMPLE 6

|  |  | g/tablet |
|---|---|---|
| Progesterone | 13.33% | 0.199 |
| Lactose Q.S. | 79.21% | 1.19 |
| Starch paste | 3.47% | 0.052 |
| Corn starch | 3.47% | 0.052 |
| Magnesium stearate | 0.52% | 0.0078 |
| Tablet weight |  | 1.5 |

EXAMPLE 7

|  |  | mg/tablet |
|---|---|---|
| Progesterone | 15.38% | 200 |
| Corn starch (binder) | 3.0% | 39 |
| Corn starch (disintegrant) | 6.0% | 78 |
| Magnesium stearate | 0.5% | 6.5 |
| Na CMC | 0.01% | 0.13 |
| PVP K 29-32 | 0.01% | 0.13 |
| Lactose | 75.38% | 979.9 |
| Aerosol OT | 0.05% | 0.65 |
| Tablet weight |  | 1.3 g |

The progesterone and lactose were blended and mixed for 15 minutes. The binder paste was then prepared by mixing 9 g corn starch with 61 ml of water containing 0.15 g aerosol OT to give a total weight of 70.15 g. From this binder mixture, 63 g was used, or 2.7% corn starch and 0.043% aerosol OT. The blended progesterone, lactose and binder paste formed a wet granulation which was passed through a #12 sieve and then put in an oven for 3 hours at 50° C. to produce a dry granulation. The dry granulation was passed through a #20 sieve, corn starch was added, and the mixture blended for 10 minutes. The sodium carboxymethylcellulose and polyvinylpyrrolidine were added to the mixture and blended for 5 minutes.

The resulting tablet weight was about 1.3 g. Maximum tablet hardness was 6 to 8 kg. The tablet disintegrated in water in 25-31 seconds, which was faster than desired.

EXAMPLE 8

| Progesterone | 20% |
| Fast flow lactose | 71.5% |
| Corn starch (binder) | 1.5% |
| Corn starch (disintegrant) | 6.0% |
| Magnesium stearate | 1.0% |

The corn starch binder paste was prepared by mixing 1.5 g corn starch with 18 ml of water. The progesterone and binder paste were wet granulated, then passed through a #12 sieve and placed in an oven for 3 hours at 50° C. The dried granulation was passed through a #20 sieve, and the fast flow lactose (which was obtained from Foremost Whey Products under product designation Fast Flo Lactose) was added. The mixture was blended for 15 minutes, the corn starch added, and then blending was continued for 5 more minutes. The magnesium stearate was added, the mixture blended for 5 more minutes, and then tablets were formed by compression.

The tablet weight was 482-490 mg, hardness was 8-9 kg, and disintegration time was 333-369 seconds. This disintegration time was within desirable ranges of 300-360 seconds. The fast flow lactose, however, produced gritty particles that were uncomfortable to the patient.

EXAMPLE 9

The same procedure was used as in Example 8, except 1.5% magnesium stearate was used instead of 1%, and 71% fast flow lactose was used instead of 71.5%. The resulting formulation was:

| Progesterone | 20% |
|---|---|
| Fast flow lactose | 71% |
| Corn starch (binder) | 1.5% |
| Corn starch (disintegrant) | 6.0% |
| Magnesium stearate | 1.5% |

The tablet weight was 490.2–500.7 g, hardness was 8.5–10.0 kg, and disintegration time in water was 250–265 seconds. Once again, however, the large particle sizes of the fast flow lactose produced a gritty suspension in the vagina that was uncomfortable to patients.

EXAMPLE 10

| Progesterone | 20% |
|---|---|
| Lactose | 70% |
| Corn starch (binder) | 3% |
| Corn starch (disintegrant) | 6% |
| Magnesium stearate | 1% |

Tablet weight was 1.0075–1.0139 g, and tablet hardness was 4.75–5.25. Disintegration time was 21–23 seconds, which was consistent with the relatively low tablet hardness. The disintegration time was much faster than the preferred 300–360 seconds.

EXAMPLE 11

| Progesterone | 15.38% |
|---|---|
| Corn starch (binder) | 3.0% |
| Corn starch (disintegrant) | 5.0% |
| Magnesium stearate | 0.8% |
| Lactose Q.S. | 75.82% |

Tablet weight was 1.33–1.41 g. Tablet hardness was 10.5–11 25 kg, and disintegration time in water was 52–60 seconds.

EXAMPLE 12

| Progesterone | 20% |
|---|---|
| Fast flow lactose | 71% |
| Corn starch (binder) | 1.5% |
| Magnesium stearate | 1.5% |
| Corn starch (disintegrant) | 6.0% |

Tablet hardness was estimated to be 8–10 kg.

EXAMPLE 13

| Progesterone | 20% |
|---|---|
| Corn starch (binder) | 1.5% |
| Fast flow lactose | 71.5% |
| Corn starch (disintegrant) | 6.0% |
| Magnesium stearate | 1.0% |

Tablet hardness was estimated to be 8–10 kg.

EXAMPLE 14

The tablet of Example 1 was also prepared by a recompression technique without the use of aqueous media. Progesterone, lactose and the corn starch in the powder form were combined with half the magnesium stearate and blended prior to making large brittle compacts (tablets). These compacts were then broken into smaller granules, combined with the remaining lubricant (magnesium stearate), and then compressed during a normal tableting procedure to make the finished dosage form. The contents of the recompressed and the single compressed tablets are essentially the same.

The tablet prepared by recompression techniques without the use of aqueous media was inferior to the tablets prepared by the method of Example 2. The recompressed tablet rapidly decomposed after insertion in the human vagina, instead of slowly disintegrating from its surface for 6–8 hours. The tablet itself was friable and brittle, and did not produce the microcrystalline dispersion described earlier for maximum bioavailability. Tablet hardness was 8–10 kg and disintegration time using USP XXI was 60–90 seconds

EXAMPLE 15

All disintegration times were determined using the USP XXI disintegration procedure (Physical Test 701) and 500 ml of buffer pH 7.4 at 37° C. In the preferred embodiments of the composition, complete disintegration occurred in the 1–6 minute range, most preferably 5–6 minute range, using the USP XXI disintegration test procedure. This time period appears to be quite rapid compared to the 6–8 hour preferred disintegration time in the human vagina. The small amount of biological fluid in the vaginal area, however, greatly prolongs the disintegration time in vivo. Significant differences in body absorption of progesterone occur between the present product and tablets or suppositories that would disintegrate in less than a minute, or even less than 4–6 minutes.

Tablets or suppositories that disintegrate in less than a minute in vitro swell rapidly in vivo, removing the surrounding fluid in the vaginal tract and decreasing the release of drug from the dosage form. The product of the present invention disintegrates by a surface erosion mechanism which is ideal for the site of administration and maximizes the efficacy and bioavailability of the progesterone.

EXAMPLE 16

The objective of this example was to clinically evaluate the safety and efficacy of a progesterone-200 mg vaginal tablet to produce a withdrawal bleed in patients with amenorrhea and functional uterine bleeding using a single daily dose of the tablet for seven consecutive days.

A total of twenty-five patients with a history of amenorrhea or functional uterine bleeding were treated with 200 mg progesterone vaginal tablets. The tablet was administered by placing it high in the vaginal vault with a vaginal applicator.

Thirteen patients (ages 20–37 years) with a history of amenorrhea and twelve patients (ages 23–44 years) with a history of functional uterine bleeding were involved in the study. All patients were evaluated for an objective response using a protocol that required a single 200 mg progesterone tablet to be inserted vaginally once daily for seven consecutive days. All patients were monitored for bioavailability of serum progesterone during the seven days of treatment. A close surveillance for toxicities was also made during the treatment and for twenty-eight days post-initiating therapy. One patient used only four tablets over a seven day period. The other twenty-four out of twenty-five patients correctly used seven tablets over seven days. The overall response from the progesterone was that twenty-five out of twenty-five had a complete withdrawal bleed response.

In evaluating responses from start of therapy (Day 1) the following was observed:

Thirteen patients with amenorrhea and twelve patients with functional uterine bleeding demonstrated withdrawal bleeding within one to eight days after the last progesterone tablet was inserted. One patient with amenorrhea and two patients with functional uterine bleeding had vaginal spotting while on therapy. A second bleed or menstrual cycle occurred twenty-four days (median) after the last tablet was inserted in twenty-two of twenty-five patients.

All patients absorbed progesterone, as indicated by the elevation of their serum levels above baseline. The mean $C_{max}$ was 12.25 ng/ml with a range of 6.9–20.6 ng/ml. The mean $t_{max}$ was 23.3 hours with a range of eight to thirty-six hours. Blood levels remained above the baseline value for 72 hours after insertion in four of the six patients. The mean area under the curve (AUC) was 350.2±52.8 ng hr/ml, with a range of 265.6–416.8 ng hr/ml. All patients experienced a withdrawal bleed four to seven days after the tablet was inserted (Mean=4.7 days).

All patients were carefully evaluated for toxicities. Extensive physical examinations and blood studies were performed during the study. No toxicities, adverse reactions or unexplained laboratory studies were observed.

Seven out of twenty-five patients had pre-therapy endometrial biopsies performed. Two patients had both pre- and post-therapy biopsies. All pre-therapy biopsies showed proliferative endometrium. One of the post-therapy biopsies showed a secretory endometrium. The other remained in a proliferative phase, but did experience a withdrawal bleeding after progesterone therapy. Several patients had minimal or no evidence of endogenous estrogen priming (vaginal cytology examinations) and, as expected, had poor absorption of progesterone as indicated by their plasma progesterone values. However, they all had a withdrawal bleeding post-therapy.

In summary, thirteen patients with amenorrhea and twelve patients with functional uterine bleeding experienced a withdrawal bleed initiated by seven days of therapy with a 200 mg progesterone vaginal tablet.

EXAMPLE 17

The objective of this study was to determine the rate and extent of absorption of a single 200 mg progesterone vaginal tablet. A secondary objective was to determine the efficacy of a single 200 mg vaginal tablet in producing a withdrawal bleed in patients with amenorrhea and functional uterine bleeding.

A total of six female patients (ages 18–30 years) with a history of amenorrhea, in the absence of organic pathology, were treated with a single 200 mg progesterone vaginal tablet. All patients had a prestudy serum progesterone level of 2 ng/ml or less.

In this bioavailability study, patients received a single 200 mg progesterone vaginal tablet at 0 hour and serum progesterone levels were sampled at 0, 0.5, 1, 1.5, 2, 4, 6, 8, 12, 24, 36, 48, and 72 hours. If the serum progesterone level had not dropped to 2.0 ng/ml or below after 72 hours, additional blood samples were taken every 24 hours until this had occurred.

Complete physical examinations were performed on visit one and then seven and twenty-eight days after the tablet was inserted. These examinations included a preliminary history, pelvic examination, and pap smear, as well as temperature, pulse, blood pressure, weight, breast examination, SMA 20, serum HCG, CBC, PT, PTT, magnesium, lipid profile, and urinalysis at each visit. At visits after the tablet was inserted, the patients were questioned to determine if they had experienced any vaginal bleeding or spotting, and the dates of such occurrences were recorded.

The results of the bioavailability study are presented in Table 1 and FIG. 4. All patients absorbed progesterone as indicated by the elevation of their serum levels above baseline. The mean $C_{max}$ was 12.25 ng/ml with a range of 6.9–20.6 ng/ml. The mean $t_{max}$ was 23.3 hours with a range of eight to thirty-six hours. Blood levels remained above the baseline value for 72 hours after insertion in four of the six patients. The mean area under the curve (AUC) was 350.2±52.8 ng hr/ml, with a range of 265.6–416.8 ng hr/ml.

TABLE 1

BIOAVAILABILITY STUDY FOR A SINGLE 200 MG PROGESTERONE VAGINAL TABLET

| | Results from Six Patients (Serum Progesterone Levels - ng/ml) | | | | | |
|---|---|---|---|---|---|---|
| Hour | LG | CW | AF | RP | CC | MF |
| 0 | 0.3 | 0.9 | 0.5 | 0.6 | 0.6 | 0.5 |
| 0.5 | 1.9 | 2.3 | 1.6 | 1.8 | 1.2 | 1.9 |
| 1 | 4.5 | 2.5 | 2.0 | 1.6 | 1.5 | 3.6 |
| 1.5 | 3.6 | 2.0 | 1.9 | 1.7 | 1.7 | 5.0 |
| 2 | 3.6 | 2.4 | 1.6 | 1.3 | 1.8 | 6.2 |
| 4 | 1.7 | 3.3 | 3.0 | 4.6 | 6.4 | 11.9 |
| 6 | 2.0 | 4.3 | 11.2 | 13.5 | 8.3 | 11.6 |
| 8 | 2.3 | 4.7 | 14.8 | 16.5 | 8.8 | 10.3 |
| 12 | 3.6 | 6.5 | 13.2 | 20.6 | 10.7 | 12.4 |
| 24 | 4.4 | 5.6 | 5.7 | 8.0 | 11.3 | 13.0 |
| 36 | 6.9 | 6.9 | 1.7 | 2.7 | 4.7 | 1.7 |
| 48 | 2.3 | 5.8 | 1.0 | 1.4 | 2.0 | 0.9 |
| 72 | 3.0 | 0.4 | 0.8 | 0.7 | 1.1 | 0.2 |
| C max | 6.9 | 6.9 | 14.8 | 20.6 | 11.3 | 13.0 |
| t max | 36 Hr | 36 Hr | 8 Hr | 12 Hr | 24 Hr | 24 Hr |
| AUC | 265.6 | 347.1 | 299.6 | 416.8 | 387.2 | 385.2 |

| | Mean +/− S.D. | Range | % C.V. |
|---|---|---|---|
| C max | 12.25 +/− 4.742 | 6.9–20.6 | 38.7 |
| t max | 23.3 Hrs | 8–36 Hrs | — |
| AUC | 350.2 +/− 52.82 | 265.6–416.8 | 15.0 |

No changes in blood chemistries or other blood values were noted while on therapy.

No adverse reactions or side effects were reported. All patients experienced a withdrawal bleed four to seven days after the tablet was inserted (Mean=4.7 days).

Tablet Disintegration Profile

Disintegration tests have shown that the vaginal tablet as formulated disintegrates by a surface erosion mechanism which ideally takes place in vivo during a four to six hour period. The micronized drug is then dispersed in the vaginal region of the body as a milky suspension, which is then absorbed.

The surface erosion mechanism is an important factor to be considered because it increases the ability of the tablet to remain in the vagina so that absorption may occur. Studies have shown that fatty acid and glycerine suppositories as they disintegrate, either by melting or by dissolution, are discharged from the vagina. Fulper, L.D., Evaluation of Vaginal Formulations of Progesterone. Masters Thesis. University of Mississippi, 1985. This lowers the bioavailability of the drug.

Because the present tablet disintegrates slowly, the drug is available in the vagina for a longer period of time and the bioavailability of the drug is increased. Therefore, as would be expected, elevated serum progesterone levels were seen 72 hours after tablet insertion resulting in a mean area under the curve (AUC) of 350.2 ng hr/ml (Table 2).

In addition, the slow decline in serum progesterone concentrations shown in the absorption profile in FIG. 4 is also typical of absorption rate-limited elimination, in which the time course of the drug in the body is a reflection of its absorption from the dosage form. This type of absorption rate-limited elimination is expected for a drug with a short half-life such as progesterone.

The results of the bioavailability study using the presently described vaginal tablet are compared with results reported by Villanueva et al. [*Fertil. Steril.* 35:433 (1981)] and Price et al. [*Fertil. Steril.* 39:490 (1983)] in Table 2.

TABLE 2
COMPARISON OF AUC OF SERUM PROGESTERONE LEVELS FOR DIFFERENT DOSAGE FORMS

| Dosage Form | Progesterone Dosage | AUC (ng hr/ml) | Hrs* | $t_{max}$ (hr) | $C_{max}$ (ng/ml) |
|---|---|---|---|---|---|
| Various Dosage Forms (5) | | | | | |
| Intramuscular injection | 50 mg. | 184 ± 42 | 24 | 14.4 | 9.52 |
| Sublingual instillation | 50 mg. | 26 ± 7 | 24 | 1.3 | 3.97 |
| Vaginal suspension | 50 mg. | 87 ± 21 | 24 | 3.0 | 7.74 |
| Vaginal Suppositories (1) | | | | | |
| Glycerinated gelatin | 25 mg. | 14.8 ± 4.7 | 24 | 2.3 | 2.52 |
| Cocoa butter | 25 mg. | 25.3 ± 3.1 | 24 | 2.2 | 6.37 |
| PEG | 25 mg. | 68.3 ± 5.0 | 24 | 3.5 | 9.72 |
| 200 mg Progesterone Vaginal Tablet | | | | | |
| Vaginal Tablet | 200 mg. | 350.2 ± 52.8 | 72 | 23.3 | 12.25 |

*Hours serum progesterone levels remained above baseline.

The 200 mg progesterone vaginal tablet yielded serum levels of progesterone for a longer period of time than the other dosage forms evaluated in the literature. Although the $C_{max}$ value for the progesterone vaginal tablet was only approximately 3 ng/ml greater than that of the injection or PEG dosage, the mean AUC after dosage with a single 200 mg tablet was twice that for an intramuscular injection and five times that of the PEG suppository. Because studies using vaginal formulations have not been able to produce elevated serum progesterone levels for greater than 24 hours, it has been postulated that choice of base affects the magnitude of serum progesterone levels, but not the total length of time progesterone levels are elevated above baseline [Price et al. (1981)]. In fact, Myers et al. suggested that all exogenous progesterone is metabolized within 24 hours [*Fertil. Steril.* 47:71 (1987)].

The present invention has demonstrated that, contrary to the expectations of those skilled in this art, blood levels can be maintained above baseline for an extended period of time merely by altering the composition of the dosage form.

Having illustrated and described the principles of my invention with reference to one preferred embodiment, it should be apparent to those persons skilled in the art that such invention may be modified in arrangement and detail without departing from such principles. I claim as my invention all such modifications as come within the true spirit and scope of the following claims.

We claim:

1. A vaginal tablet which disintegrates from its surface after insertion in the vagina and comprises:
   a binder selected from the group consisting of particulate starch and polyvinylpyrrolidone,
   a disintegrant selected from the group consisting of corn starch, rice starch, wheat starch and potato starch,
   progesterone, lactose, binder and disintegrant formulated in sufficient amounts and particle sizes to deliver progesterone above basal blood levels for 48 to 72 hours after the tablet is inserted into a human vagina.

2. The vaginal tablet of claim 1 wherein the tablet forms a fine milky suspension when it disintegrates.

3. The vaginal tablet of claim 1 wherein said tablet further comprises a lubricant.

4. The vaginal tablet of claim 1 wherein said tablet comprises 13.5% progesterone by weight and 79% lactose by weight.

5. The vaginal tablet of claim 4 wherein said tablet comprises 7% starch by weight as the binder and disintegrant.

6. The vaginal tablet of claim 5 wherein said tablet comprises 3.5% starch by weight as a binder and 3.5% starch by weight as a disintegrant.

7. The vaginal tablet of claim 6 wherein said lactose and progesterone are bound by the starch binder in a granule, and said starch disintegrant surrounds said granule.

8. The vaginal tablet of claim 1 further comprising a lubricant.

9. The vaginal tablet of claim 8 wherein said lubricant comprises less than 1% by weight of the tablet.

10. The vaginal tablet of claim 9 wherein said lubricant is magnesium stearate.

11. A vaginal tablet comprising:
    a therapeutic amount of progesterone,
    a lactose excipient bound to the progesterone in a ratio of 6:1 by weight of progesterone to lactose,
    a disintegrant,
    and a binder in a ratio of 1:1 by weight of disintegrant to binder, the lactose, progesterone, disintegrant and binder being present in sufficient amounts and particle sizes to deliver progesterone above basal blood levels for at least about 48 hours after the tablet is inserted into a human vagina, the binder being selected from the group consisting of particulate starch and polyvinylpyrrolidone, the disintegrant being selected from the group consisting of corn starch, rice starch, wheat starch and potato starch.

12. The vaginal tablet of claim 11 wherein said progesterone, excipient and disintegrant are present in sufficient amounts to provide release of progesterone by surface erosion of the tablet.

13. The vaginal tablet of claim 12 wherein the starch is corn starch.

14. The vaginal tablet of claim 12 wherein the excipient is hydrophilic.

15. The vaginal tablet of claim 14 wherein the starch binder is corn starch paste.

16. A vaginal tablet comprising, by weight, about 13-20% progesterone, 65-85% lactose, 5-20% starch and 0.1-0.9% lubricant.

17. The vaginal tablet of claim 16 wherein the 5-20% starch includes 2-10% starch paste by weight as a binder and 3-10% starch by weight as a disintegrant.

18. The vaginal tablet of claim 17 wherein the tablet comprises 12-14% progesterone, 78-81% lactose, 2-4% starch paste binder, 2-4% starch disintegrant, and 0.4-0.6% lubricant.

19. The vaginal tablet of claim 18 wherein the tablet comprises 13.5% progesterone, 79% lactose, 3.5% binder, 3.5% disintegrant, and 0.52% lubricant.

20. The vaginal tablet of claim 16 wherein the lubricant is magnesium stearate.

21. The vaginal tablet of claim 17 wherein the starch is corn starch.

22. The vaginal tablet of claim 18 wherein the starch is corn starch and the lubricant is magnesium stearate.

23. A vaginal tablet comprising, by weight, 13.5% progesterone, 79% lactose, 3.5% corn starch paste binder, 3.5% corn starch disintegrant, and 0.52% magnesium stearate.

24. The vaginal tablet of claim 23 wherein said tablet is in the shape of a diamond.

25. The vaginal tablet of claim 1 wherein the tablet is 2.5 cm long, 1.3 cm wide, and 0.5 cm thick.

26. A vaginal tablet comprising progesterone and lactose particles in a ratio by weight of 1:6 in sufficient amounts to deliver above basal levels of progesterone after the tablet is inserted into a human vagina, at least 80% of the progesterone particles being less than a micron in diameter, and the lactose particles substantially all being less than 50 microns in diameter, the tablet further comprising a binder selected from the group consisting of particulate starch and polyvinylpyrrolidone, and a disintegrant selected from the group consisting of corn starch, rice starch, wheat starch and potato starch, the binder and disintegrant being present in a weight ratio of 1:1.

27. The tablet of claim 26 wherein the lactose particles are comprised of hydrous lactose.

28. A vaginal tablet comprising progesterone and lactose particles in sufficient amounts and particle sizes to deliver above basal blood levels of progesterone after the tablet is inserted into a human vagina, and a suitable binder means and disintegrant means for delivering above basal blood levels of progesterone for at least 48 hours after the tablet is inserted into a human vagina.

29. The tablet of claim 28 wherein the disintegrant means further comprises starch particles.

30. The tablet of claim 29 wherein said starch particles are selected from the group consisting of corn starch, rice starch, wheat starch and potato starch.

31. The tablet of claim 28 wherein at least 80% of the progesterone particles are less than a micron in diameter.

32. The tablet of claim 29 wherein the lactose particles and starch particles are less than 50 microns in diameter.

33. The tablet of claim 28 wherein the ratio of progesterone to lactose is 1:6.

34. The tablet of claim 29 wherein the lactose and progesterone are bound by the starch in a granule, the starch disintegrant surrounding the granule.

* * * * *